United States Patent [19]
Lunt

[11] 4,382,303
[45] May 10, 1983

[54] NON-WOVEN POLYESTER WEARING APPAREL

[76] Inventor: Audrey T. Lunt, 6371 Vermont Hill Rd., South Wales, N.Y. 14139

[21] Appl. No.: 814,915

[22] Filed: Jul. 12, 1977

Related U.S. Application Data

[63] Continuation-in-part of Ser. No. 760,169, Jan. 17, 1977, abandoned.

[51] Int. Cl.³ .............. A41B 13/06; A41D 11/00; A41D 13/12
[52] U.S. Cl. .................. 2/114; 2/69.5; 2/75; 2/80; 2/83
[58] Field of Search .......... 2/74, 75, 114, 80, 69.5, 2/83; 156/73.1

[56] References Cited

U.S. PATENT DOCUMENTS

| | | | |
|---|---|---|---|
| 782,819 | 2/1905 | Biklé | 2/114 X |
| 1,462,515 | 7/1923 | McElroy | 2/114 X |
| 2,576,812 | 11/1951 | Siegel | 2/80 |
| 2,598,462 | 5/1952 | Strauss | 2/69.5 |
| 2,622,248 | 12/1952 | Schaye | 2/80 |
| 2,677,130 | 5/1954 | O'Hayer | 2/114 X |
| 3,078,467 | 2/1963 | Artzt | 2/114 X |
| 3,111,676 | 11/1963 | Artzt et al. | 2/83 X |
| 3,435,461 | 4/1969 | Artzt | 2/83 |
| 3,783,061 | 1/1974 | Hahn | 156/73.1 |
| 3,817,802 | 6/1974 | Meyer | 156/73.1 X |
| 3,911,499 | 10/1975 | Benevento et al. | 2/114 |

OTHER PUBLICATIONS

"For the Carriage Trade", P.N.R. #106, 1/5/70.

*Primary Examiner*—Rodney H. Bonck
*Attorney, Agent, or Firm*—Michael Ebert

[57] ABSTRACT

A basic garment suitable for use as a medical examination gown or for other purposes calling for apparel which may be quickly opened to fully expose the body of the wearer. The garment is fabricated from a single blank of non-woven polyester sheet material contoured to define front and rear sections having complementary sleeve portions, with a transverse fold line therebetween in the center of which is a neck opening. The front section is slit into a pair of panels that separate at the neck opening whereby when the front section is folded over the rear section and the two sections are ultrasonically seamed together at their opposing side margins, a garment is created having the desired characteristics. The front panels are releasably held together by hook and loop nylon fabric fasteners whose male components are ultrasonically-bonded to the margin of one panel and whose female components are ultrasonically-bonded to the margin of the other panel.

2 Claims, 10 Drawing Figures

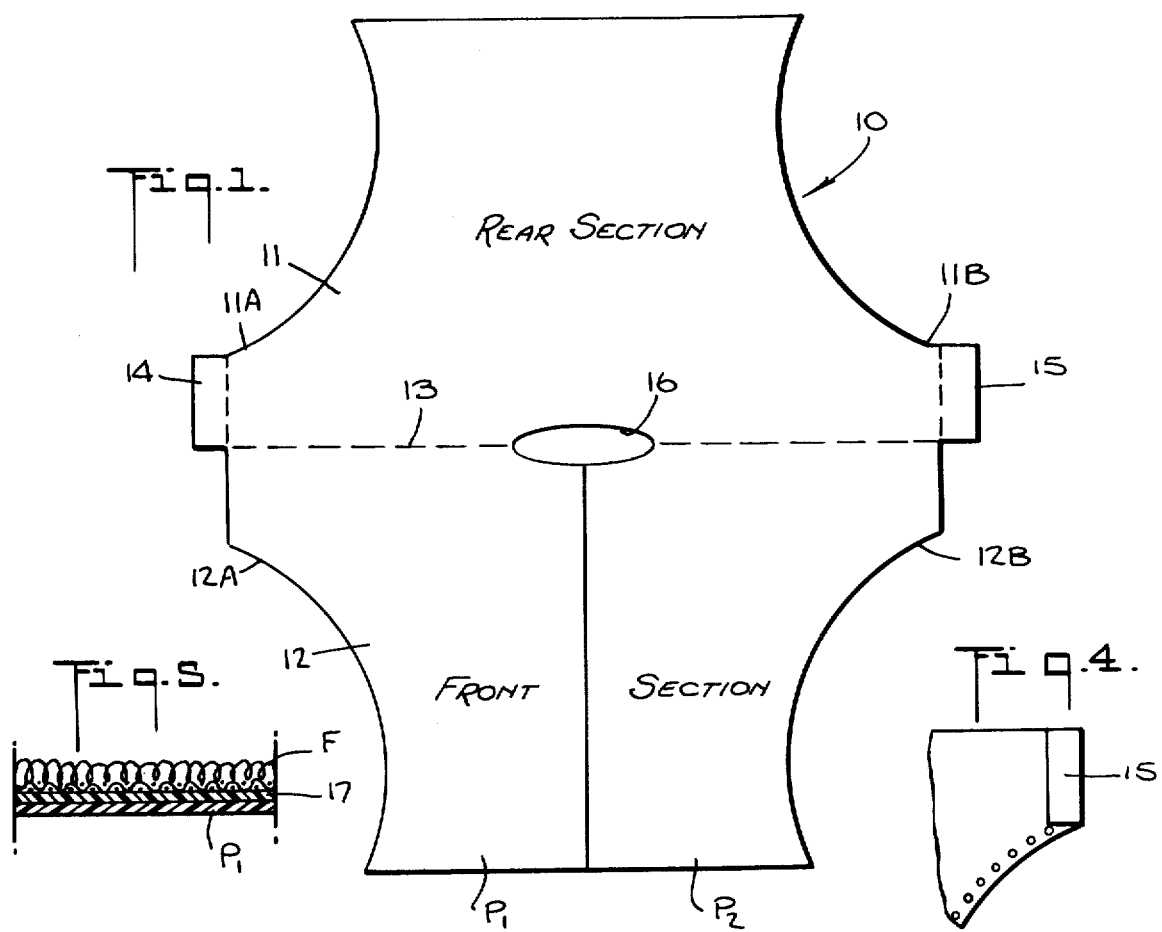
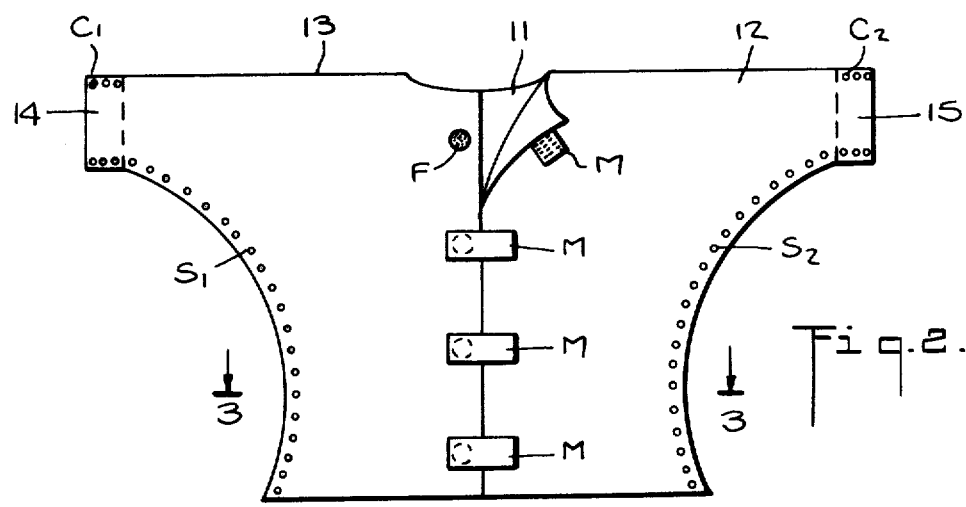
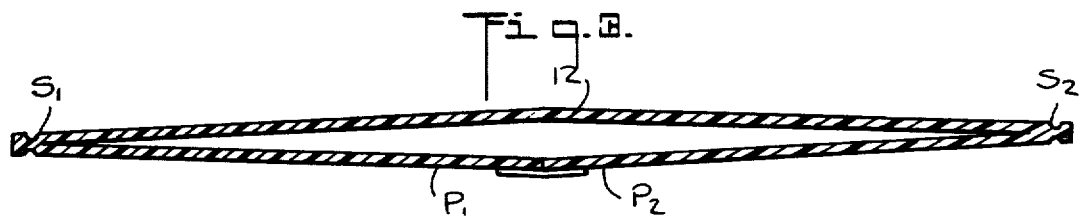

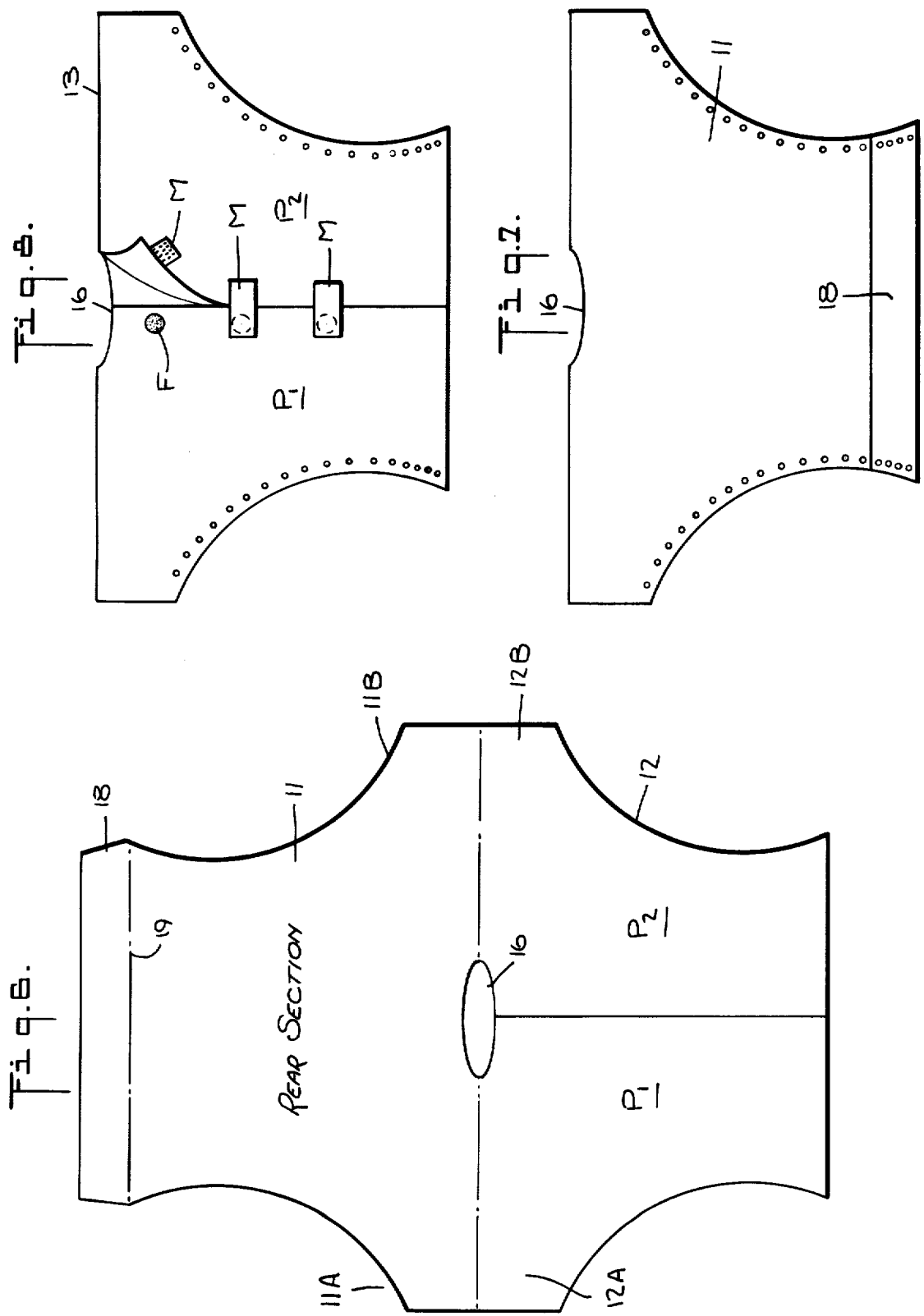

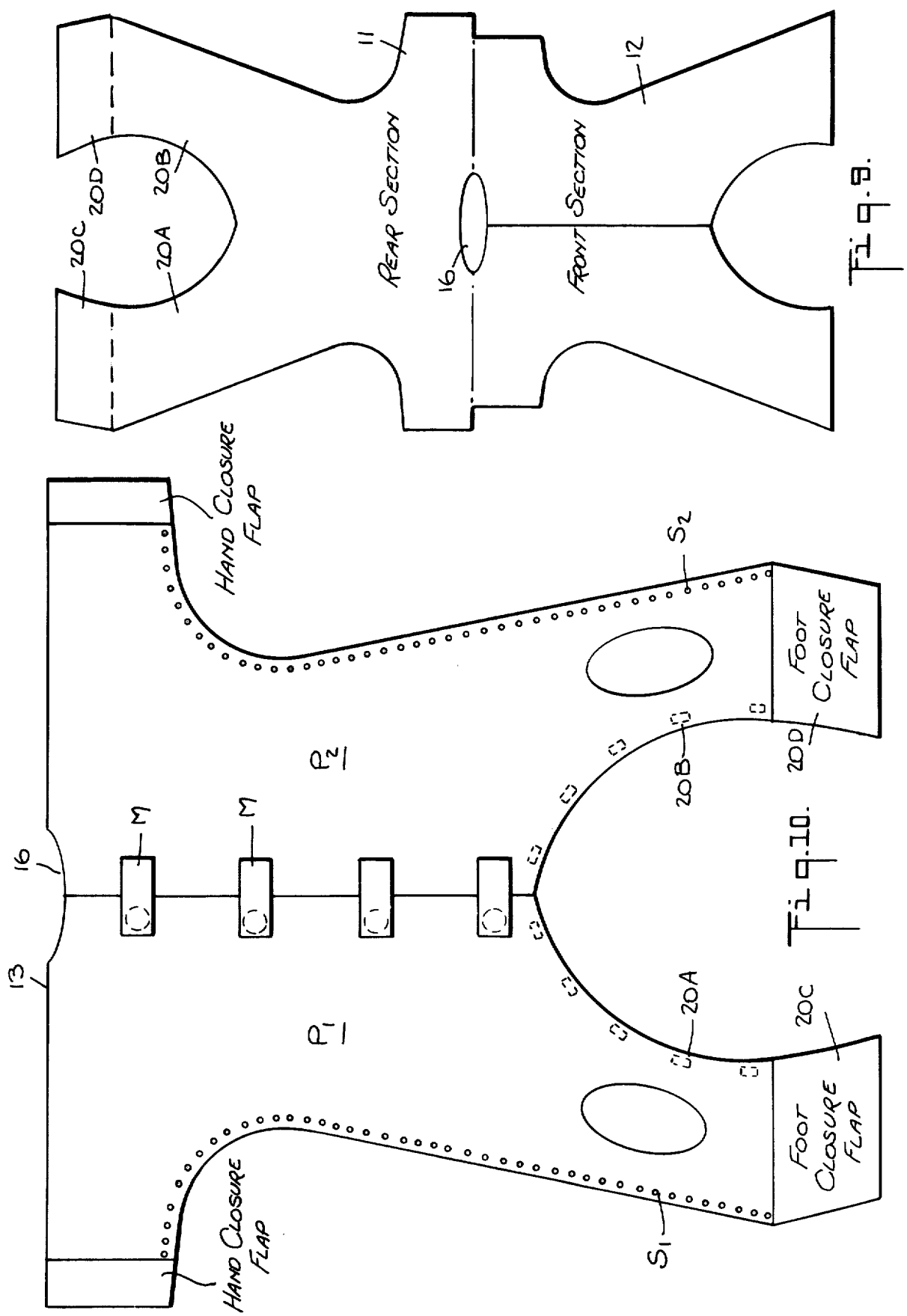

NON-WOVEN POLYESTER WEARING APPAREL

This application is a continuation-in-part of my copending application Ser. No. 760,169, filed Jan. 17, 1977 and now abandoned, entitled "Medical Examination Garments for Infants," the entire disclosure of this copening application being incorporated herein by reference.

BACKGROUND OF INVENTION

This invention relates generally to wearing apparel fabricated of non-woven synthetic fiber material, and more particularly to a medical examination garment for infants created from a single blank of non-woven polyester sheet material.

While the invention will be described in connection with medical examination garments for infants, it will be appreciated that the principles underlying the invention are applicable to adult size medical examination gowns and other low-cost articles of apparel designed to be quickly opened to fully expose the body of the wearer.

In my copending application Ser. No. 585,973, there is disclosed a medical examination garment for infants made of three pieces of synthetic fabric or non-woven paper material which are sewed or otherwise seamed together, use being made of a relatively soft material similar to that used for diapers. The advantage of a garment of the type disclosed in my copending application is that it is adapted to sheath an infant's body in a manner insuring adequate warmth and the absence of drafts, the garment shielding the entire body from contact with dirt and surfaces capable of causing injury, while protecting bandaged areas of the body. A significant feature of this garment is that it can be quickly opened to fully expose the entire body for medical examination.

From the practical standpoint, a garment of the type disclosed in my copending application is relatively difficult and expensive to make, for it is necessary to cut the basic stock material into three pieces and to then seam the pieces together, after which one must attach fasteners thereto. In order to facilitate quick examination of an infant patient with minimum disturbance to the child, the use of synthetic fabric hook and loop fasteners is desirable, for such closures can be released quickly without difficulty. However, it has not heretofore been feasible to ultrasonically bond such closures, which are formed of nylon, to polyester fabric of the type suitable for infant garments.

SUMMARY OF INVENTION

In view of the foregoing, it is the main object of this invention to provide wearing apparel formed from a single blank of non-woven synthetic plastic sheeting, the garment having ultrasonically-welded seams.

Also an object of the invention is to provide a garment of the above type which is fabricated of non-woven polyester material to which hook and loop nylon fasteners are ultrasonically welded.

A salient feature of the invention resides in the use of ultrasonic welding as the sole means of effecting seaming of the garment as well as the attachment of the fasteners thereto, thereby eliminating the need for sewing or adhesive bonding and other assembly steps which add substantially to the cost of producing the garment.

An important aspect of the invention is that even though the hook and loop fasteners are formed of nylon, whereas the fabric to which it is to be attached is a non-woven polyester which normally is incompatible with a nylon fastener, ultrasonic welding is effected by means of an intermediate web adapted to reconcile the differences between the nylon fastener and the polyester fabric.

Yet another object of this invention is to provide a technique for forming garments of a single blank of sheeting material, which technique is applicable to the creation of different articles of apparel such as infant undershirts, gowns and crawlers.

Briefly stated, these objects are attained in an article of apparel formed from a single blank of non-woven polyester sheeting contoured to define front and rear sections having complementary sleeve portions, with a fold line therebetween in the center of which is a neck opening.

The front section is slit into a pair of panels that separate at the neck opening whereby when the front section is folded over the rear section and the two sections are ultrasonically seamed together at their opposing side margins, a garment is created having the desired characteristics. The front panels are releasably held together by hook and loop nylon fabric fasteners whose male components are ultrasonically-bonded to the margin of one panel and whose female components are ultrasonically-bonded at corresponding positions to the margin of the other panel.

To effect ultrasonic welding of the nylon components to the polyester surface, use is made of an intermediate web of nylon having a heat-activatable adhesive coated on one face thereof, the nylon web engaging the nylon component of the fastener and the adhesive face abutting the polyester surface whereby the heat created by ultrasonic energy causes the nylon web to fuse to the nylon component and to activate the adhesive to effect bonding to the polyester surface.

The rear section of the blank may be provided with a foot extension which is folded over to form a protective pocket whose ends are ultrasonically seamed to the opposing sides of the rear section. Alternatively, the front and rear sections may be formed with complementary leg extensions whereby the resultant garment is provided with leg sleeves and serves as a crawler.

OUTLINE OF DRAWINGS

For a better understanding of the invention as well as other objects and further features thereof, reference is made to the following detailed description to be read in conjunction with the accompanying drawings, wherein:

FIG. 1 is a plan view of a single blank from which an infant's surgical examination gown in accordance with the invention is created;

FIG. 2 illustrates, in front view, the surgical examination gown;

FIG. 3 is a transverse section taken in the plane indicated by line 3—3 in FIG. 2;

FIG. 4 is a detail showing the sleeve cuff of the gown;

FIG. 5 is a section through the female component of a fabric fastener which is ultrasonically-bonded to a polyester substrate;

FIG. 6 is a plan view of the blank for forming a gown having a protective foot pocket in accordance with the invention;

FIG. 7 is a rear view of this pocketed gown;

FIG. 8 is a front view of this pocketed gown;

FIG. 9 illustrates the blank for forming a crawler in accordance with the invention; and FIG. 10 is a front view of the crawler.

DESCRIPTION OF INVENTION

First Embodiment

Referring now to FIG. 1, there is illustrated a blank 10 from which an infant's medical examination gown is created, the blank being formed of non-woven sheeting constituted entirely of randomly-dispersed polyester fibers, preferably of the type known commercially under the trademark NEXUS manufactured by Burlington Industries.

This polyester material is relatively soft and satisfies Federal standards for non-flammability. The Nexus material is non-toxic and non-allergenic, and is sterilizable in laundering. Though a garment made of this material in the manner of the present invention is of low cost and therefore expendable, for purposes of economy the garment may be reused, in that it may be safely washed repeatedly and sterilized. The nature of the seaming and the quality of the fasteners are such, as will later be explained, as to resist rupture even under vigorous laundry processing.

In practice, the contoured blank 10 may be mass-produced by die cutting the blanks from a continuous web of non-woven polyester material or from a stack of sheets formed of this material. The dies used for this purpose also serve to cut the neck opening and the slit in the blank, so that the only other steps involved in producing the blank are the folding and ultrasonic welding operations.

Blank 10 has a generally cruciform profile to define a rear section 11 and a similarly-shaped front section 12, the line of demarcation between these sections being a fold line indicated by dotted line 13. The ends of the transverse portion of the cruciform are stepped to define sleeve portions 11A and 11B of back section 11, and complementary sleeve portions 12A and 12B of front section 12. Sleeve portions 11A and 11B are longer than sleeve portions 12 and 12B to form cuff-flaps 14 and 15 whose fold lines are indicated by dotted lines.

An elliptical hole 16 is cut into the blank at the center of fold line 13 to form a neck opening. Front section 12 is slit down its middle, the slit extending from neck opening 16 to the lower edge of the section, thereby dividing the front section into left and right panels $P_1$ and $P_2$.

To create a medical examination gown from this blank, front section 12 is folded over rear section 11 along line 13, as shown in FIG. 2, and the opposing side of the folded piece are ultrasonically-welded along the curved opposing side margins $S_1$ and $S_2$ to produce seams which extend from the bottom edge to the end of the sleeve.

Cuff flaps 14 and 15 are folded behind the rear section sleeve portions 11A and 11B and ultrasonically-welded thereto at the margins of the sleeve at $C_1$ and $C_2$. In this folded back position of the cuffs, the arms of the infant may be extended through the sleeves. But where it is desirable to seal off the sleeves, the cuffs may be brought forward and folded over the front, as shown in FIG. 4.

To releasably hold panels $P_1$ and $P_2$ together, a set of four hook and loop fabric fasteners are provided, each constituted by a male or hook component M created by a uniform array of stiff hooks, and a female or loop component F whose surface is constituted by a pile of tiny soft loops. When pressed together, the hooks become embedded in the loops and held thereby until the components are peeled apart. The male components are ultrasonically-sealed to the margin of panel $P_2$, and the female components M are similarly sealed at corresponding positions to the margins of panel $P_1$.

Hook and loop fasteners of the type known commercially as VELCRO fasteners are snag and jam-proof and washable. They are available in tape form which can be cut to a desired size or die-cut into various shapes. The hook component is woven in the form of raised loops which are heat set to retain their shape, the loops then being cut to form the hooks. The loop component is formed by a ground tape interwoven with a dense multiplicity of yarns to form a pile surface that is then napped to create a continuous, disoriented mass of uncut loops designed to engage with the male loops.

Both components are fabricated of nylon, and this creates a problem in attaching these components to the polyester non-woven surface of the panels. While some success was experienced in ultrasonically welding the hook component to the polyester material, it was not possible to fuse the loop component thereto; for nylon and polyester have dissimilar thermal characteristics, and a setting of the ultrasonic welding machine appropriate for polyester material is improper for nylon.

Ultrasonic welding may be used to seam together two or more sheets of thermoplastic material, this being accomplished by introducing the sheets between a "sonotrode" and an anvil. The sonotrode is caused to vibrate at an ultrasonic frequency and exerts an oscillatory pressure on the sheets, whereby ultrasonic energy is transformed into heat. This heat softens the thermoplastic sheets and causes them to fuse together. The amount of heat generated is controlled by the adjustable amplitude of ultrasonic vibration.

No problem is experienced in welding together sheets having about the same or identical melting points. Thus if the sheets are fabricated of fibers of nylon 66, a polyamide polymer whose melting point is 264° C., the ultrasonic equipment must be set to take this factor into account. But if one seeks to seam together a nylon tape to a thermoplastic fabric having a significantly different melting point, then the setting of the machine for nylon may be inappropriate to the other material, and will either inadequately heat the other material or excessively heat and degrade this material, depending on the nature of the difference between the two sheets.

To effect ultrasonic bonding in accordance with the invention, the nylon female loop component F is provided at its underside with a web 17 of polyester material having a heat-activatable adhesive layer thereon which is in contact with the component F, the polyester web engaging the polyester panel $P_1$. Hence when ultrasonic energy is applied to this assembly, the polyester web is fused to the polyester panel, whereas the adhesive is activated to effect a secure bond between the web and the female component F.

Thus the same ultrasonic equipment which is used to effect seaming of the garment serves also to apply the hook and loop fasteners thereto, thereby minimizing production time and costs. It will be appreciated that the one-piece design for this instant wear is totally threadless, yet washable--an advantage lacking in non-woven garments which require gluing to assemble.

The same basic one-piece design can be used to create an undershirt rather than a gown, the difference therebetween residing only in the length of the garments, the undershirt being shorter than the gown. In the case of an undershirt, only two closures are necessary rather than three or four on a longer article of apparel.

Second Embodiment

The second embodiment of the invention is essentially the same as the first embodiment, except that, as shown in FIGS. 6, 7 and 8, the sleeves are without cuffs, and the rear section 11 is provided with a common foot extension 18 above a fold line 19.

When rear section 11 is folded behind front section 12, the foot extension 18 is then folded over the rear section, as shown in FIG. 8, and ultrasonically welded thereto at its margins to create a foot pocket which normally is not in use. But when one wishes to eliminate the need for a receiving blanket, the foot pocket is brought forward to enclose the feet of the infant, as shown in FIG. 7.

Third Embodiment

Referring now to FIGS. 9 and 10, there is shown a crawler made from a one-piece blank which mainly differs from that in FIG. 1 in that the rear section is provided with a pair of foot extensions 20A and 20B, and the front section is provided with complementary foot extensions 21A and 21B. Hence, when the rear section is folded behind the front section, foot sleeves are formed which are enclosed by means of hook and loop fabric fasteners. The rear foot sections are provided with closure flaps 20C and 20D.

Thus when all the hook and loop fasteners are released, the entire body of the wearer, including the feet, is exposed. In practice, the knees of the foot sleeves may be reinforced by patches.

While there have been shown and described preferred embodiments of non-woven polyester wearing apparel in accordance with the invention, it will be appreciated that many changes and modifications may be made therein without, however, departing from the essential spirit thereof.

I claim:

1. A basic garment suitable for use as a medical examination gown or for other purposes calling for apparel which may be quickly opened to fully exposé the body of the wearer, said garment being fabricated of a single blank of non-woven synthetic fiber material formed of sterilizable polyester sheeting contoured to define front and rear sections having complementary sleeve portions, with a fold line therebetween in the center of which is a neck opening, said front section being slit along a line extending from the neck opening to the lower end of the front section to define a pair of panels in edge-abutting relation that separate at the neck opening, the rear section being folded behind the front section and the two sections being ultrasonically welded together at their opposing side margins, and a plurality of hook and loop fabric fasteners whose male components are ultrasonically bonded to the margins of one panel at spaced positions therealong, the male components overlapping the edge of said one panel, and whose female components are ultrasonically bonded to the margin of the other panel at corresponding spaced positions at which the female components are engageable by the overlapping male components, whereby the panels may be opened to expose the body of the wearer or closed to protect the body, said fastener components being formed of nylon, and at least one of said components being ultrasonically bonded to said polyester through an intermediate polyester web having a heat-activatable adhesive layer in contact with the nylon component whereby when ultrasonic energy is applied, the polyester web is fused to the polyester sheeting and the adhesive is activated to effect an adhesive bond between the web and the nylon component.

2. A garment as set forth in claim 1, wherein said rear section is provided with a common foot extension which is folded behind said rear section and ultrasonically welded thereto at its margins to define a foot pocket that is normally not in use but which may be folded forward to enclose both feet of the wearer.

* * * * *